(12) United States Patent
Bohdy

(10) Patent No.: US 11,071,955 B1
(45) Date of Patent: Jul. 27, 2021

(54) NANOPLASMOID SUSPENSIONS AND SYSTEMS AND DEVICES FOR THE GENERATION THEREOF

(71) Applicant: Charlles Bohdy, Sheffield Village, OH (US)

(72) Inventor: Charlles Bohdy, Sheffield Village, OH (US)

( * ) Notice: Subject to any disclaimer, the term of this patent is extended or adjusted under 35 U.S.C. 154(b) by 150 days.

(21) Appl. No.: 15/619,368

(22) Filed: Jun. 9, 2017

Related U.S. Application Data

(60) Provisional application No. 62/347,635, filed on Jun. 9, 2016.

(51) Int. Cl.

| | | |
|---|---|---|
| *B01F 3/04* | (2006.01) |
| *A61K 47/69* | (2017.01) |
| *B01F 13/00* | (2006.01) |
| *A61Q 19/00* | (2006.01) |
| *A61P 17/00* | (2006.01) |
| *A61K 8/02* | (2006.01) |

(52) U.S. Cl.
CPC ........ *B01F 3/04106* (2013.01); *A61K 8/0204* (2013.01); *A61K 47/6925* (2017.08); *A61P 17/00* (2018.01); *A61Q 19/00* (2013.01); *B01F 3/04468* (2013.01); *B01F 13/0094* (2013.01)

(58) Field of Classification Search
CPC .............. B01F 3/04106; B01F 13/0094; B01F 3/04468; A61K 47/6925; A61K 8/0204; A61P 17/00; A61Q 19/00
See application file for complete search history.

(56) References Cited

U.S. PATENT DOCUMENTS

| | | | |
|---|---|---|---|
| 3,319,106 A | 5/1967 | Hertz | |
| 4,023,065 A | 5/1977 | Koloc | |
| 4,599,158 A * | 7/1986 | Ofenloch | .................. C25B 1/04 |
| | | | 204/229.5 |
| 4,891,150 A | 1/1990 | Koloc | |
| 5,015,432 A | 5/1991 | Koloc | |
| 5,041,760 A | 8/1991 | Koloc | |
| 8,317,165 B2 | 11/2012 | Yamasaki et al. | |
| 2007/0189972 A1 | 8/2007 | Chiba | |
| 2007/0286795 A1 | 12/2007 | Chiba | |

(Continued)

FOREIGN PATENT DOCUMENTS

| | | |
|---|---|---|
| EP | 2116589 | 11/2009 |
| WO | 2014184585 | 1/2015 |
| WO | 2015048904 | 4/2015 |

OTHER PUBLICATIONS

Versteegh et al, "Long-Living Plasmoids from an Atmospheric Water Discharge" Plasma Sources Sci. and Tech. 17(2) (May 2008).

(Continued)

*Primary Examiner* — Stephen Hobson
(74) *Attorney, Agent, or Firm* — Fish IP Law, LLP

(57) ABSTRACT

Systems, devices, and methods are provided that are useful in generating a fluid suspension of nanoplasmoid bubbles. Such systems utilize a nanobubble/nanoplasmoid generator in conjunction with mechanisms for applying energy to the fluid in the form of electrolytic events, pressure waves, electrical fields, and/or magnetic fields. The nanobubble/nanoplasmoid generator is of modular construction that is readily adaptable to a wide variety of applications. Various applications of nanoplasmoid bubble suspensions so produced are described.

14 Claims, 15 Drawing Sheets

(56) References Cited

U.S. PATENT DOCUMENTS

2009/0051055 A1    2/2009  Park
2013/0034829 A1    2/2013  Choi
2014/0116889 A1*  5/2014  Nakamoto ............ C02F 1/4618
                                                                            205/556
2014/0120167 A1    5/2014  Lapotko et al.

OTHER PUBLICATIONS

Dubowsky et al, "Infrared Emission Spectroscopy of Atmospheric-Pressure Ball Plasmoids" J. Mol. Spec. 322: 1 to 8 (2016).

* cited by examiner

NANOPLASMOID SUSPENSIONS AND SYSTEMS AND DEVICES FOR THE GENERATION THEREOF

This application claims priority to U.S. Provisional Application No. 62/347,635 filed on Jun. 9, 2016. These and all other referenced extrinsic materials are incorporated herein by reference in their entirety. Where a definition or use of a term in a reference that is incorporated by reference is inconsistent or contrary to the definition of that term provided herein, the definition of that term provided herein is deemed to be controlling.

FIELD OF THE INVENTION

The field of the invention is generation of plasmoids, in particular in association with nanobubble suspensions.

BACKGROUND

The following description includes information that may be useful in understanding the present invention. It is not an admission that any of the information provided herein is prior art or relevant to the presently claimed invention, or that any publication specifically or implicitly referenced is prior art.

Plasmoids are, essentially, collections of ionized atoms or molecules (i.e. a plasma) bounded by an electrical field, and consequently a magnetic field. Typically plasmoids have an approximately cylindrical structure, however toroidal and spherical configurations are known. Plasmoids occur naturally on an astronomical scale (for example, in the sun's corona) and on smaller scales under certain conditions (for example, "ball lightening"). Short lived plasmoids on the centimeter scale can also be generated using conventional household items, such as microwave ovens.

Attempts have been made to generate stable plasmoids in a controlled fashion, particularly for potential use in fusion generators. Devices to generate such plasmoids typically involve application of an external field to an annular (see U.S. Pat. No. 3,319,106, to Hertz) or coiled (see U.S. Pat. No. 4,023,065, to Koloc; U.S. Pat. No. 4,891,180 to Koloc; U.S. Pat. No. 5,015,432 to Koloc; and U.S. Pat. No. 5,041,760 to Koloc) magnetic and/or electrical field source. All publications identified herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply. Such approaches, however, require constant energy input (in the form of the externally applied field) to maintain the plasmoid. In contrast, relatively simple devices utilizing a ring-shaped electrode have been shown to generate relatively long-lived spherical plasmoids on a centimeter scale through capacitive discharge (see Versteegh et al, "Long-Living Plasmoids from an Atmospheric Water Discharge" Plasma Sources Sci. and Tech. 17(2) (May 2008); Dubowsky et al, "Infrared Emission Spectroscopy of Atmospheric-Pressure Ball Plasmoids" J. Mol. Spec. 322:1 to 8 (2016)). The taught devices however, do not show consistent performance as many discharge events fail to produce observable plasmoids.

More recently, United States Patent Application Publication No. 2014/120167 (to Lapotko et al) taught the therapeutic value of "plasmonic nanobubbles" produced by irradiation of gold nanoparticles that demonstrate surface plasmon resonance when exposed to certain wavelengths. Such plasmonic nanobubbles are, however, very short lived and require the use of a potentially dangerous near infrared laser source.

It is, however, possible to generate stable nanobubbles (i.e. bubbles having a mean diameter of less than 1 µm) in a liquid. Such bubbles lie in a size range that provides stability, as they are small enough to be subject to Brownian motion and tend to accumulate surface charges that reduce aggregation and subsequent fusion. For example, EP Patent Application No. 2116589 (to Shiode) describes a system that utilizes a pump to force a fuel-containing liquid through a nozzle or porous structure that is in immediate proximity to a surface that is oriented perpendicular to flow exiting the nozzle. The resulting shear forces generate a suspension of nanobubbles. United States Patent Application No. 2009/051055 (to Park) utilizes a pressure-driven system that forces water through a series of spiral and disc-shaped "net members" to generate nanobubble suspensions. United States Patent Application Publication No. 2010/038244 (to Wood et al) shows a device that generates nanobubbles containing charged oxygen species using a device that forces fluid through a chamber containing a stator and a rotor. The fluid moves through a set of minute holes in either the stator or the rotor to generate oxygen-containing nanobubbles as the rotor spins. The inventors claim that the device produces an electrokinetic fluid with physical, chemical, and biological properties that are distinct from conventional oxygenated fluids. United States Patent Application Publication No. 2013/0034829 (to Choi) describes a device that incorporates a venture to generate "nanobubbles" in a suspension used for oral irrigation, however the disclosed device appears to generate bubbles having a diameter of around 100 µm—which are too large to be considered nanobubbles. Such devices and methods, however, either fail to provide true nanobubbles or fail to provide a high concentration of nanobubbles.

PCT Application Publication No. WO2014/184585 (to Govind and Foster) describes a device that incorporates a number of different technologies for generation of fine bubbles connected in series to provide a single nanobubble generating system that can, reportedly, generate "a few hundred thousand" nanobubbles per $cm^3$. The design of the device is complex, however. This is due in part to differing pressure and flow rate requirements for the interconnected technologies. U.S. Pat. No. 8,317,165 (to Yamasaki et al) similarly utilizes a system of serially connected bubble generators that utilize shear, pressure-solution, high speed stirring, and/or swirling flow to generate bubble containing suspensions. As taught, however, significant concentration of inorganic salts must be present. Similarly, United States Patent Application Publication No. 2007/0189972 (to Chiba and Takahashi) and United States Patent Application Publication No. 2007/0286795 (to Chiba and Takahashi) discuss methods for reducing microbubbles to nanobubbles through application of various stresses (such as mechanical shear, ultrasound, and high voltage electrostatic discharge) to microbubble suspensions that include significant concentrations of specified salts.

PCT Application Publication No. WO2015/048904 (to Bauer) describes a device that utilizes a series of cavitation zones separated by shear planes to generate a nanobubble suspension. The device utilizes a series of notched discs arranged at intervals along a central rod, with the sharp-edged notches offset from each other on each pair of such discs. In some embodiments an electrical potential is applied to an insulated rod that is placed within the liquid flow in order to alter the zeta potential of the nanobubbles so generated. The inventors state that the nanobubble suspension generated by the device, which can contain up to about $5 \times 10^8$ nanobubbles per mL, has "increased paramagnetic qualities" and an increased ORP relative to untreated water.

Thus, there is still a need for methods, systems, and/or devices that can generate small plasmoids, such as plasmoids having a major diameter of less than about 1 μm.

SUMMARY OF THE INVENTION

The inventive subject matter provides apparatus, systems and methods in which a nanoplasmoids are generated in a fluid. Gases used to generate such nanoplasmoids can be supplied to or generated from the fluid (for example, by electrolysis). Systems and devices can include a source of energy for the generation of plasmoids (such as a microwave, radio frequency, or ultrasound source) and a modular shearing section arranged in a flow path of the fluid. The modular shearing section can be arranged as a series of individual shearing modules or slices along a common flow path, and can be expanded to accommodate different scales of operation. Such a modular arrangement advantageously simplifies reconfiguration and/or redesign of the device (for example, by incorporation of new shearing modules or slices) without the need for redesign.

One embodiment of the inventive concept is a system for generating a nanobubble/nanoplasmoid suspension, which includes an electrolytic cell, a nanobubble/nanoplasmoid generator configured to form a suspension of a second fluid in a first fluid wherein elements of the second fluid in the suspension have a mean diameter of less than 1 μm, and that is fluidically coupled to the electrolytic cell, and a source of a pressure differential that is in fluid communication with the electrolytic cell and the nanobubble/nanoplasmoid generator. The source of the pressure differential is positioned and configured to move the first fluid through the system. In some embodiments the first fluid is a liquid and the second fluid is a gas. In some embodiments the system can include a reservoir that receives a nanoplasmoid bubble suspension from the nanobubble/nanoplasmoid generator.

In some embodiments the nanobubble/nanoplasmoid generator includes a first vortex mixing plate that includes a first central circular cavity and a first aperture in fluid communication with the first central circular cavity, where the first aperture is configured as an asymmetric folium having a first narrow terminus and where the first narrow terminus is oriented in a first radial direction relative to the first central circular cavity. It can also include a shear mixing plate that includes a second aperture that is in fluid communication with the first central circular cavity, where the second aperture includes a second narrow terminus and where the second narrow terminus is fluidically coupled to a shear mixing segment. Such a shear mixing segment can include a first shear region that includes a first narrow inlet, a first expansion region, and a first narrowed outlet, along with a second shear region that includes a second narrow inlet fluidically coupled to the first narrow outlet, a second expansion region, and a second narrow outlet. It can also include a second vortex mixing plate that includes a second central circular cavity and a third aperture in fluid communication with the first shear mixing plate and the second central circular cavity, where the third aperture is configured as an asymmetric folium having a third narrow terminus and the third narrow terminus is oriented in a second radial direction relative to the second central circular cavity. It can also include a third center vortex plate that includes a third central circular cavity and a fourth aperture in fluid communication with the second central circular cavity and the third central circular cavity, where the fourth aperture is configured as an asymmetric folium having a fourth narrow terminus and the fourth narrow terminus is oriented in a third radial direction relative to the third central circular cavity, and where the third radial direction is in opposition to the second radial direction. It can also include an inlet plate in fluid communication with a source of a first fluid, a source of a second fluid, and the first vortex mixing plate.

In some embodiments the shear mixing plate includes a plurality of shear mixing segments, where the plurality of shear mixing segments is serially arranged such that, with the exception of a terminal shear mixing segment, each of the second narrow outlets is fluidically coupled to the first narrow outlet of a subsequent one of the plurality of shear mixing segments, and wherein the plurality of shear mixing segments are arranged in a spiral fashion.

In some embodiments the first vortex mixing plate is juxtaposed with a first distribution plate comprising a first port, and wherein the first distribution plate is juxtaposed with the shear mixing plate. In other embodiments the shear mixing plate is juxtaposed with a second distribution plate comprising a second port, and wherein the second distribution plate is juxtaposed with the second vortex mixing plate. In still other embodiments the second vortex mixing plate is juxtaposed with a third distribution plate comprising a third port, and wherein the third distribution plate is juxtaposed with the third vortex mixing plate.

In some embodiments of the inventive concept the third center mixing plate is in fluid communication with a nozzle. In such embodiments the nozzle includes an expansion chamber that is in fluid communication with the third center mixing plate, a nozzle outlet, and a central constriction interposed between the expansion chamber and the nozzle outlet.

Systems of the inventive concept can include a field source configured to generate a field that intersects the first fluid. Such a field source can be an electrical field source and/or a magnetic field source. Such a system can include a controller that is communicatively coupled to the field source and configured to modulate the field (for example, application of a waveform).

Another embodiment of the inventive concept is a system for generating a nanobubble/nanoplasmoid suspension that includes a pressure transducer, a nanobubble/nanoplasmoid generator configured to form a suspension of a second fluid in a first fluid, and that is fluidically coupled to the pressure transducer, and a source of a pressure differential that is in fluid communication with the pressure transducer and the nanobubble/nanoplasmoid generator, where the source of the pressure differential is positioned and configured to move the first fluid through the system. In such a system the first fluid can be a liquids and the second fluid can be a gas. In some embodiments the system include reservoir that receives a nanoplasmoid bubble suspension from the nanobubble/nanoplasmoid generator.

In such a system the nanobubble/nanoplasmoid generator can include a first vortex mixing plate that includes a first central circular cavity and a first aperture in fluid communication with the first central circular cavity, where the first aperture is configured as an asymmetric folium having a first narrow terminus and where the first narrow terminus is oriented in a first radial direction relative to the first central circular cavity. It can also include a shear mixing plate that includes a second aperture that is in fluid communication with the first central circular cavity, where the second aperture includes a second narrow terminus and where the second narrow terminus is fluidically coupled to a shear mixing segment. Such a shear mixing segment can include a first shear region that includes a first narrow inlet, a first expansion region, and a first narrowed outlet, along with a second shear region that includes a second narrow inlet fluidically coupled to the first narrow outlet, a second expansion region, and a second narrow outlet. It can also include a second vortex mixing plate that includes a second central circular cavity and a third aperture in fluid communication with the first shear mixing plate and the second central circular cavity, where the third aperture is configured as an asymmetric folium having a third narrow terminus and the third narrow terminus is oriented in a second radial direction relative to the second central circular cavity. It can also include a third center vortex plate that includes a third central circular cavity and a fourth aperture in fluid communication with the second central circular cavity and the third central circular cavity, where the fourth aperture is configured as an asymmetric folium having a fourth narrow terminus and the fourth narrow terminus is oriented in a third radial direction relative to the third central circular cavity, and where the third radial direction is in opposition to the second radial direction. It can also include an inlet plate in fluid communication with a source of a first fluid, a source of a second fluid, and the first vortex mixing plate.

In some embodiments the shear mixing plate includes a plurality of shear mixing segments, where the plurality of shear mixing segments is serially arranged such that, with the exception of a terminal shear mixing segment, each of the second narrow outlets is fluidically coupled to the first narrow outlet of a subsequent one of the plurality of shear mixing segments, and wherein the plurality of shear mixing segments are arranged in a spiral fashion.

In some embodiments the first vortex mixing plate is juxtaposed with a first distribution plate comprising a first port, and wherein the first distribution plate is juxtaposed with the shear mixing plate. In other embodiments the shear mixing plate is juxtaposed with a second distribution plate comprising a second port, and wherein the second distribution plate is juxtaposed with the second vortex mixing plate. In still other embodiments the second vortex mixing plate is juxtaposed with a third distribution plate comprising a third port, and wherein the third distribution plate is juxtaposed with the third vortex mixing plate.

In some embodiments of the inventive concept the third center mixing plate is in fluid communication with a nozzle. In such embodiments the nozzle includes an expansion chamber that is in fluid communication with the third center mixing plate, a nozzle outlet, and a central constriction interposed between the expansion chamber and the nozzle outlet.

Systems of the inventive concept can include a field source configured to generate a field that intersects the first fluid. Such a field source can be an electrical field source and/or a magnetic field source. Such a system can include a controller that is communicatively coupled to the field source and configured to modulate the field (for example, application of a waveform).

Such a system can include a frequency generator that is communicatively coupled to the pressure transducer and configured to transmit a frequency (e.g. an ultrasonic frequency) to the pressure transducer. Such a system can include a second controller that is communicatively coupled to the frequency generator and configured to modulate the frequency (such as application of a waveform).

Another embodiment of the inventive concept is a method of preparing a beverage that includes nanoplasmoid bubbles, using a system as described above. In such an embodiment the first fluid can include water, and the second fluid can be a gas derived from electrolysis.

Another embodiment of the inventive concept is a method of preparing a therapeutic suspension that includes nanoplasmoid bubbles, using a system as described above. In such an embodiment the first fluid can include water, and the second fluid can be a gas derived from electrolysis.

Another embodiment of the inventive concept is a method of treating a skin condition that includes providing a nanobubble/nanoplasmoid suspension, and contacting an affected skin area with the nanobubble/nanoplasmoid suspension on a treatment schedule effective to treat the skin condition (such as topical fungal infections, wounds, wrinkles, abnormally dry skin, eczema, psoriasis, and/or skin carcinoma). Such a nanobubble/nanoplasmoid suspension is provided in a reservoir configured for immersion of at least the affected skin area. The treatment schedule includes contacting the affected skin area with the nanobubble/nanoplasmoid suspension for a period of at least 20 minutes (or, alternatively, 5 minutes to two hours), at a frequency of from three times a day to once a month (or, alternatively, four times a day to once a month). In some embodiments such treatments can continue for 30 to 90 days.

BRIEF DESCRIPTION OF THE DRAWINGS

FIG. 1A depicts such a system where a pump is interposed between an electrolytic cell and a nanobubble/nanoplasmoid generator. FIG. 1B depicts such a system where an electrolytic cell is interposed between a pump and a nanobubble/nanoplasmoid generator.

FIG. 6A depicts a cross section of a vortex mixing plate. FIG. 6B depicts an orthogonal view of a vortex mixing plate.

FIG. 7A depicts a cross section of a shear mixing plate. FIG. 7B depicts an orthogonal view of a shear mixing plate.

FIG. 8A depicts a distribution plate with a central aperture. FIG. 8B depicts a distribution plate with a peripheral aperture.

FIG. 9A depicts a cross section of a shear mixing plate. FIG. 9B depicts an orthogonal view of a shear mixing plate.

FIG. 10A depicts a view through an expansion chamber of a nozzle. FIG. 10B depicts a side view of a nozzle. FIG. 10C depicts an orthogonal view of a nozzle.

FIG. 13A depicts results of particle characterization studies of distilled water prior to treatment. FIG. 13B depicts results of particle characterization studies of distilled water following treatment.

DETAILED DESCRIPTION

Figure 1A:
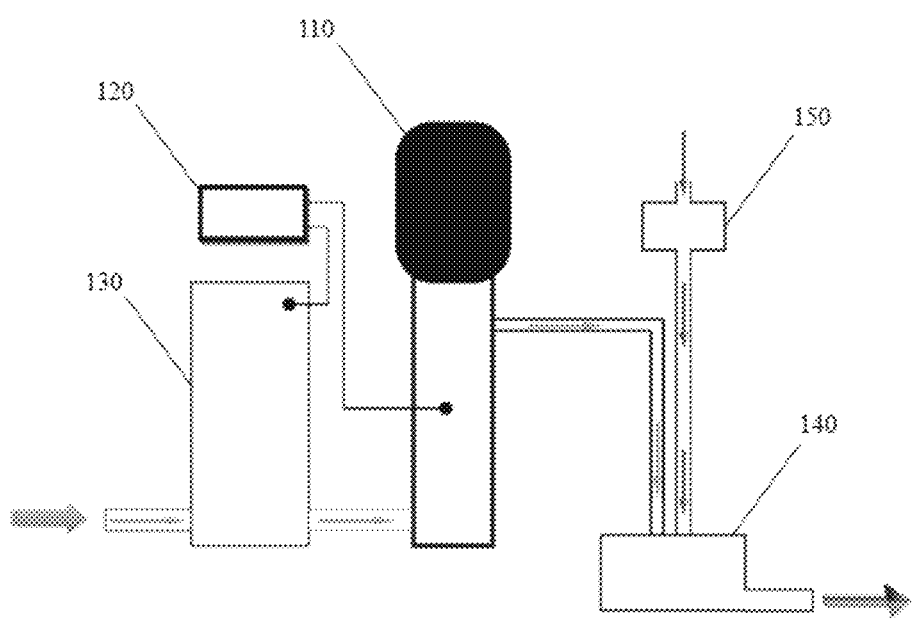
FIGS. 1A and 1B depict embodiments of a system of the inventive concept that include an electrolytic cell.

Systems, devices and methods are described that generate nanoplasmoids (i.e. plasmoids having a diameter of 1 µm or less across a major axis). A nanoplasmoid so generated within or encapsulated by a nanobubble (i.e. a bubble having a diameter or less than about 1 µm) forms a nanoplasmoid bubble (i.e. a nanobubble currently or formerly containing a nanoplasmoid). Systems and devices for generating nanoplasmoid bubbles include a nanobubble generator, a field source, and a device for generating a pressure differential that moves a fluid through the system or device. In some embodiments the fluid is recirculated through the system or device. Suitable field sources include an electrolytic cell, an electrical field generator, a magnetic field generator, and an ultrasound source. Application of a field generated by a field source to a fluid undergoing nanobubble generation results in the formation of nanoplasmoid bubbles formed from a nanobubble that incorporates one or more nanoplasmoid(s). In a preferred embodiment nanoplasmoids so generated have a toroidal configuration.

Various objects, features, aspects and advantages of the inventive subject matter will become more apparent from the following detailed description of preferred embodiments, along with the accompanying drawing figures in which like numerals represent like components.

One should appreciate that the systems, devices, and methods described herein provide a safe, effective, and efficient method for generating nanoplasmoids, nanoplasmoid bubbles, and/or nanobubbles of controlled size and composition, which have been shown to have numerous useful applications described below.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The recitation of ranges of values herein is merely intended to serve as a shorthand method of referring individually to each separate value falling within the range. Unless otherwise indicated herein, each individual value with a range is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

Systems and methods of the inventive concept allow for the generation of nanoplasmoids in fluid suspensions, using virtually any gas at the nano-scale. This is distinct from conventional nanobubble generation, and utilizes a combination of processes to induce charge and plasma formation to effectively and efficiently generate suspensions of these nanoscopic plasmoids, for use in a variety of applications.

Embodiments of the inventive concept can accomplish this nanoplasmoid generation using microwave and/or radio frequencies (preferably in combination), coupled with application of electrical energy (e.g. amperage and/or voltage). For example, microwave energy can be applied to a fluid being processed at one or more wavelength(s) ranging from 1 mm to 1 meter. Similarly, radio frequencies can be applied to a fluid being processed at one or more frequency(ies) ranging from 3 kHz to 300 kHz. In some embodiments electromagnetic energy is applied at frequencies ranging from 3 kHz to 600 MHz, and/or octaves of frequencies within this range. The amplitude and/or the wavelength of applied microwave and/or radio frequency energy can be modulated during application. Such a modulation can be patterned, for example as a regular pattern of increasing or decreasing amplitude and/or frequency. Such a regular pattern can describe a continuous ramp or waveform, or can be intermittent (e.g. as bursts or pulses). Suitable waveforms include sine waves, step waves, and superwaves. Suitable bursts or pulses can range in duration from 1 μsec to 5 or more minutes. In a preferred embodiment such microwave and/or radio frequency energy is applied to the fluid as it flows past one or more suitable emitters. In such embodiments the pattern utilized for modulating such microwave and/or radio frequency energy can be modulated to adjust for changes in the flow rate of the fluid.

Nanoplasmoids of the inventive concept can be generated while passing through one or more (e.g. a series) of shearing zones, where nanotization occurs. Devices and systems of the inventive concept provide a capacity for a varied or indefinite number of shearing zones to be configured together to increase the travel of the fluid through the zone as well as allowing for implementation of more than one shearing mechanism. This can be accomplished by coupling individual shearing modules together along a common fluid flow path. Such a variable configuration advantageously permits incorporation of different and/or new shear modules, and allows new shearing designs to be added without changing or redesigning the entire system or device. Such a configuration also allows for ease of disassembly for cleaning and/or service of the device or system.

Systems and devices of the inventive concept can include one or more reservoir(s), water reaction chamber(s), and/or section(s), where fluid is stored and/or mixed with a gas that is intended for nanoplasmoid generation. In some embodiments such a gas or gases can be generated from the fluid itself, for example using electrolytic and/or sonocavitational methods. In some embodiments the stored fluids are able to be recirculated through the device, allowing for generation of higher concentrations of the nanoplasmoids to be generated. In other embodiments it can be a pass-through or single pass section.

Systems and devices of the inventive concept can include one or more plasma generating mechanism(s) or section(s). Suitable plasma generating mechanisms can include a microwave source, a radio frequency source, an acoustic energy source, and/or an electrolytic device. Such a mechanism allows for the generation of nanoplasmoids without resorting to excessive heat and/or pressure, resulting in generation of charged gas that can be sheared, while being charged. A plasma generating mechanism relies on an individual element as described above or a combination of such elements charge gasses being introduced. In aqueous applications it also can allow for the splitting of water and generation or liberation of gasses from the water itself. Such a plasma generating section can provide amplification of sonocavitation-derived plasmoids generated in a shearing mechanism or section. Surface charges generated in such a section can provide stable plasmoids.

Accordingly, systems and devices of the inventive concept can include one or more generator cell(s) and or transformer(s). Suitable generator cells include microwave, radio frequency, acoustic wave, and/or electromagnetic field producing mechanisms or combination thereof that power the plasma generating mechanism. Success has been achieved in generating plasmoids using such elements, both individually in some embodiments or in combination in others. In some aqueous embodiments this allows for the splitting of the water and generation of hydrogen and oxygen, and charging such gasses to produce plasmoids.

As noted above, preferred embodiments of the inventive concept can process a fluid flow. Such embodiments can include a fluid circulating system. The fluid circulating system can include a pump or pumps used pressurize or create vacuum, and serve propel the fluids or draw the fluids into cavitation inducing and/or shearing zone(s) of the system or device. Plasmoids have been successfully generated using a pressure system, a vacuum system, and a combination of the two in push/pull and pull/push arrangements. This allows for the fluids to be treated in a single pass or to be re-circulated. It also allows for oils to be introduced for the manufacture of nanoplasmoid emulsions.

Systems and devices of the inventive concept can include one or more shearing zones. Such shearing zones can be arranged as a series of modules, providing for an expandable, variably configurable shearing mechanism. For example, such a configurable shearing mechanism can be arranged as a series of cavitation inducing modules or slices that are able to coupled in series (e.g., by being stacked and coupled together, for example by bolts or applied pressure) along a fluid flow path in order to provide a series of shearing zones in a contiguous chamber, section, and/or tunnel. Such shearing zones allow fluids to be forced into a rotation and counter-rotation-like turbulence, inducing further size reduction of the plasmoids generated using the plasma generating mechanism. Sonocavitation can also produced in such a portion of the system or device. In embodiments in which the shearing zone is made up of individual modules or slices that, when combined, produce the entire geometry of the section, modular design allows for continuing development testing and introduction of new or novel geometries without resorting to the design and creation of an entirely new device. The length of such a shearing zone can be increased or decreased as the desired output's needs require. This portion of the system or device provides not only shearing but also nanotizing and mixing the fluids gasses (and, in the case of nanoplasmoid emulsions, an oil).

Systems and devices of the inventive concept can include one or more processors or controllers. Suitable processors or controllers include a printed circuit board (PCB Board), programmable logic control timing and/or switching mechanisms, and analog timing and/or switching mechanisms. Such a controller or control module allows for both monitoring and real time feedback and adjustment or control of the various components, including modulation of frequency, amplitude, signal voltage, amperage, pressure, flow rate, etc. Nanoplasmoids have been produced using systems and devices having analog or digital automatic controllers, as well as devices and systems with a programmable timer switch. Such controllers can allow for intelligent programming and interaction between various parts and or components or systems.

Systems and devices of the inventive concept can include one or more gas mixing mechanisms. Such gas mixing mechanisms allow the desired gas(ses) to be introduced while being mixed into the fluid. Suitable mechanisms include but are not limited to venture mixers, static mixers, venturi/static mixer combinations, nanobubbler(s), a structuring vortexer, tubes or tubules, and/or one or more membranes(s). This mechanism or series of mechanisms allows for mixing to occur by thoroughly mixing gas into the fluid either in a tank or reservoir or series of tanks or reservoirs or via a mixing section in a continuous flow operation.

Systems and devices of the inventive concept can include one or more "rocket" structuring mixing nozzle(s). Such a nozzle can be coupled within the fluid flow path to either the beginning or the end of the shearing section. Alternatively, such a nozzle can coupled within the fluid flow path at both the beginning of the shearing section and a second nozzle coupled within the fluid flow path at the end of the shearing section. In appearance and function the rocket structuring mixing nozzle is similar to the outlet nozzle of a conventional liquid rocket engine (without ignition). Such a nozzle sends the resulting fluid into, out of, or into then out of the shearing section of the device in a vortex mixing pattern. This has the effect of structuring or ordering the fluids and the nanotized plasma gasses on the way into or out of the device.

One embodiment of a system of the inventive concept is shown in FIG. 1A. As shown, the system includes a nanobubble/nanoplasmoid generator (140) and an electrolytic cell (130), which is in turn connected to a power supply (120). Fluid, impelled by a pump (110) that provides a pressure differential, moves through the electrolytic cell (130) and a nanobubble/nanoplasmoid generator (140), which can optionally include an input (150) for a gas. Suitable electrolytic cells can include a cathode and an anode, which are arranged so that the products of electrolysis (for example, $O_2$, $H_2$, OH−, $OH^-$, H+, etc.) are released into the circulating fluid. Such species can react with one another to generate other species, for example peroxides. In some embodiments an electrolyte, such as NaCl, can be included in the fluid and be acted upon by the electrolytic cell to produce species derived from the electrolyte (such as HCl, NaOH, $Cl_2$, etc.). In some embodiments of the inventive concept the system or device can include a sensor that detects or quantifies species produced by the electrolytic cell, and a controller that receives data from the sensor. In such embodiments the presence and/or concentration of a product of electrolysis can be monitored using the sensor, with such data monitored by the controller which in turn modulates the power supplied to the electrolytic cell in order to maintain the rate of electrolysis within a desired range. For example, a pH monitor can be used to determine the amount of OH− and/or H+ present in the circulating fluid, and the power supplied to the electrolytic cell modulated to maintain the pH within a desired range. Products of the electrolysis of electrolytes or salts present in the circulating fluid can be monitored in a similar fashion.

An electrolytic cell utilized in a system of the inventive concept can have any suitable configuration. For example, an electrolytic cell can be configured as a reservoir that includes at least one anode and at least one cathode, and can include features that increase the surface area of the anode and/or cathode. For example, an anode and/or cathode can be provided with one or more holes, configured as a mesh, have a roughened surface, and or include a nanocoating. Such an anode or cathode can be configured as plate, coil, rod, disc, sphere, or any suitable shape. Alternatively, an electrolytic cell can be configured as a pipe or tube through which fluid moves in passing through the system. In such an embodiment the pipe or tube can include one or more anode and/or cathode. Such anodes and cathodes can be in the form of an electrode that intrudes into the path of fluid flow. Alternatively, such anodes and cathodes can be integrated into or form part of a wall of the pipe or tube. In still other embodiments such anodes and cathodes can have a cylindrical conformation similar to that of the pipe or tube, but having a smaller diameter and positioned centrally within the pipe or tube. In still other embodiments anodes and/or cathodes can be incorporated into or form part of a mixing plate (such as those described below), such that cavitation and electrolysis are performed essentially simultaneously. In a preferred embodiment the electrolytic cell is provided as a coiled pipe or tube having a first diameter, within which at least one anode and at least one cathode are provided in the form of cylinders having second and third diameters that are smaller than the first diameter. In such an embodiment an anode and cathode pair can be provided as set of nesting cylinders arranged around a common central axis, with one of either the anode and cathode having a smaller diameter than the other member of the pair.

Figure 1B:
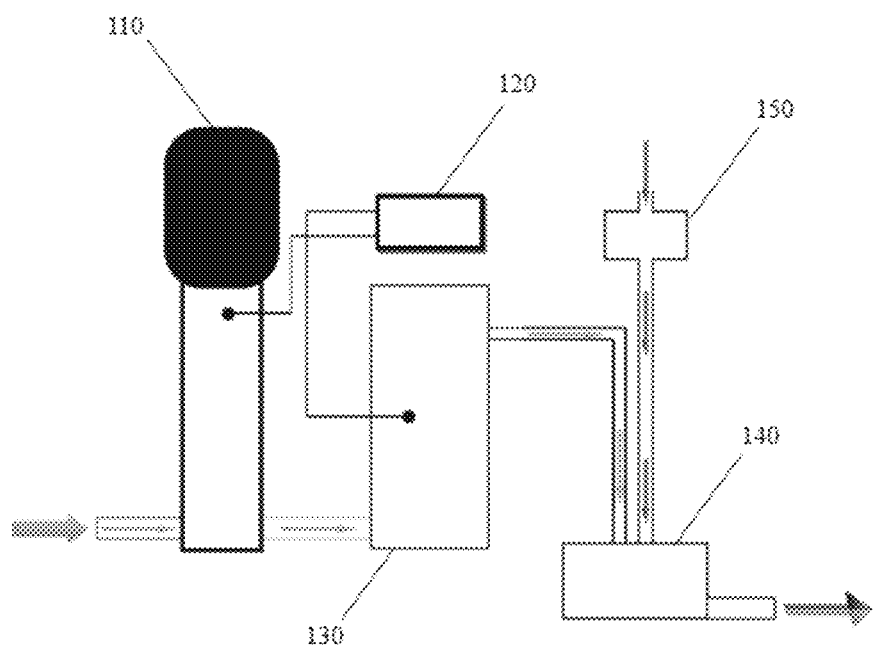

The cathode and/or anode of the electrolytic cell can be arranged so that species produced by only one of the cathode or anode are released into circulating fluid. It should be appreciated that such species, notably charged species, can accumulate on the surface of nanobubbles and nanobubble plasmoids and enhance stability through charge repulsion. Electrodes of the electrolytic cell can be made of any suitable material, including stainless steel, copper, bronze, gold, silver, platinum, and conductive polymers. Such materials can enter the circulating fluid during electrolytic processing and be subsequently integrated into nanoplasmoid bubbles. In some embodiments the output from the nanobubble generator is coupled to the fluid input of the electrolytic cell, channeling some or all of the output back through the system. An alternative arrangement is shown in FIG. 1B, in which an electrolytic cell (130) is placed between a pump (110) or other source of pressure differential and a nanobubble/nanoplasmoid generator (140).

As noted above, in some embodiments the nanobubble generator is provided with a gas in addition to the circulating fluid. Such a gas can be provided from a reservoir (such as a pressurized tank) or generated in situ (for example, by electrolysis or treatment of air with zeolites). Suitable gases include air, $O_2$, $H_2$, $N_2$, CO, $CO_2$, HOH, and noble gases. Such gases can be incorporated into nanobubbles and hence into nanoplasmoids of nanoplasmoid bubbles.

Figure 2:
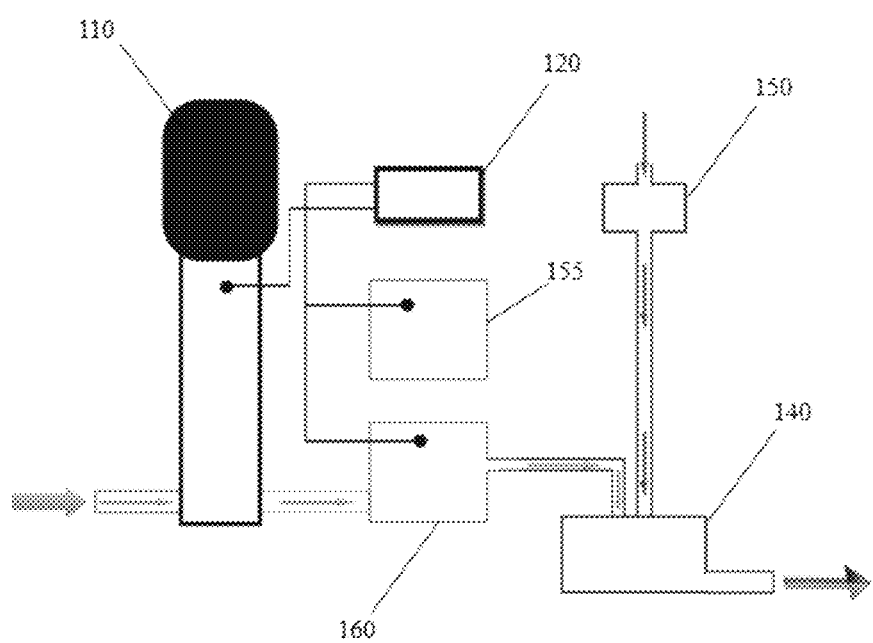
FIG. 2 depicts an embodiment of a system of the inventive concept that includes a transducer and a nanobubble/nanoplasmoid generator.

Another embodiment of a system of the inventive concept is shown in FIG. 2. As shown, the system includes a nanobubble/nanoplasmoid generator (140) and a pressure transducer (160) that is coupled to a frequency generator (150). Such a frequency generator (150) can provide an oscillating electrical potential to the transducer (160), which in turn applies corresponding pressure waves to fluid circulating through the system. The oscillating electrical potential can be provided in any suitable waveform, for example as a sinusoidal or sigmoidal wave function, a stepped wave function, or a combination thereof. Such a waveform would be imparted, at least in part, to the corresponding pressure wave provided by the transducer. In a preferred embodiment the oscillating electrical potential results in corresponding pressure waves generated at ultrasonic frequencies. Suitable transducer include contact transducers (for example, vibrating plates) and immersion or probe transducer that are introduced into the path of the flowing fluid. Such transducers can utilize piezoelectric and/or magnetostrictive elements in order to transform the applied electrical potential to a pressure wave. A power supply (120) is provided that supplies power to components such as a pump (110), frequency generator (155), and/or transducer (160).

Fluid, impelled by a pump (110) that provides a pressure differential, moves through or past the transducer (160) and a nanobubble/nanoplasmoid generator (140), which can optionally include an input (150) for a gas. Such a gas can be provided from a reservoir (such as a pressurized tank) or generated in situ (for example, by electrolysis or treatment of air with zeolites). Suitable gases include air, $O_2$, $H_2$, and $N_2$. Such gases can be incorporated into nanobubbles and hence into nanoplasmoids of nanoplasmoid bubbles. In some embodiments of the inventive concept the system or device can include a sensor (such as a microphone) that detects or characterizes the pressure waves applied by the transducer sensor. In such embodiments characteristics (such as amplitude, frequency, etc.) of the pressure waves can be monitored using the sensor, with such data monitored by the controller which in turn modulates the frequency generator in order to maintain the pressure waves within a desired range or set of ranges. Similarly, temperature of the fluid in the system can be monitored (for example, suing a thermometer or infrared sensor) and temperature data supplied to a controller that can modulate the frequency generator and/or activate a cooling system to maintain temperature of the fluid within a desired range. Such a cooling system (not shown in FIG. 2) can be a compression-based cooling system, a thermoelectric cooling system, an evaporative cooling system, or a combination of these.

Figure 3:
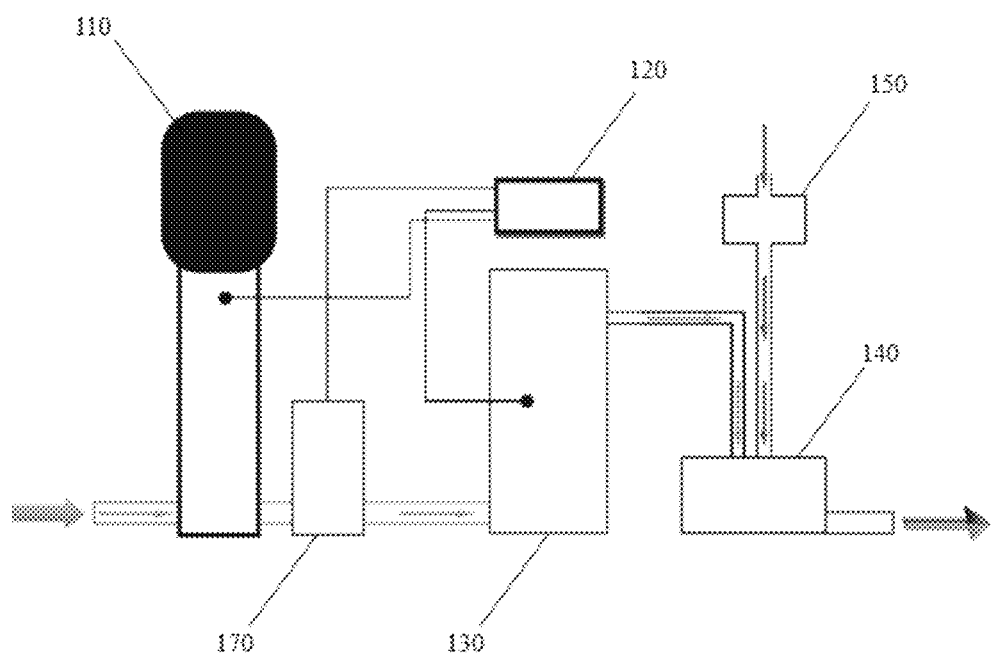
FIG. 3 depicts an embodiment of a system of the inventive concept that includes a magnetic field source and a nanobubble/nanoplasmoid generator.

Another embodiment of a system of the inventive concept is shown in FIG. 3. As shown, the system includes a nanobubble/nanoplasmoid generator (140), a source of a magnetic field (170), and an electrolytic cell (130). A power supply (120) is provided that supplies power to a pump (110) and/or to the magnetic field source (170), if needed. Fluid, impelled by a pump (110) that provides a pressure differential, moves through a magnetic field applied by the magnetic field source (170), an electrolytic cell (130), and a nanobubble/nanoplasmoid generator (140), which can optionally include an input (150) for a gas. Suitable sources for the magnetic field can be permanent magnets and/or electromagnets. In embodiments that incorporate an electromagnet, a controller can be used to modulate the applied magnetic field. In such embodiments the magnetic field can be applied continuously, periodically, and/or varied in a systematic manner, for example applying the magnetic field at varying strengths and/or polarization over time. Such variations can be periodic, for example with magnetic field strength and/or polarization oscillating as a waveform. Suitable waveforms include sinusoidal or sigmoidal waves, stepped wave functions, or combinations thereof.

As noted above, such embodiments that include a magnetic field source can include an electrolytic cell. Suitable electrolytic cells can include a cathode and an anode, which are arranged so that the products of electrolysis (for example, $O_2$, $H_2$, OH–, $OH^-$, H+, etc.) are released into the circulating fluid. Such species can react with one another to generate other species, for example peroxides. In some embodiments an electrolyte, such as NaCl, can be included in the fluid and be acted upon by the electrolytic cell to produce species derived from the electrolyte (such as HCl, NaOH, $Cl_2$, etc.). In some embodiments of the inventive concept the system or device can include a sensor that detects or quantifies species produced by the electrolytic cell, and a controller that receives data from the sensor. In such embodiments the presence and/or concentration of a product of electrolysis can be monitored using the sensor, with such data monitored by the controller which in turn modulates the power supplied to the electrolytic cell in order to maintain the rate of electrolysis within a desired range. For example, a pH monitor can be used to determine the amount of OH– and/or H+ present in the circulating fluid, and the power supplied to the electrolytic cell modulated to maintain the pH within a desired range. Products of the electrolysis of electrolytes or salts present in the circulating fluid can be monitored in a similar fashion.

The cathode and/or anode of the electrolytic cell can be arranged so that species produced by only one of the cathode or anode are released into circulating fluid. It should be appreciated that such species, notably charged species, can accumulate on the surface of nanobubbles and nanobubble plasmoids and enhance stability through charge repulsion. Electrodes of the electrolytic cell can be made of any suitable material, including stainless steel, copper, bronze, gold, silver, platinum, and conductive polymers. Such materials can enter the circulating fluid during electrolytic processing and be subsequently integrated into nanoplasmoid bubbles. In some embodiments the output from the nanobubble generator is coupled to the fluid input of the electrolytic cell, channeling some or all of the output back through the system.

An electrolytic cell utilized in a system of the inventive concept can have any suitable configuration. For example, an electrolytic cell can be configured as a reservoir that includes at least one anode and at least one cathode. Such an anode or cathode can be configured as plate, coil, rod, disc, sphere, or any suitable shape. Alternatively, an electrolytic cell can be configured as a pipe or tube through which fluid moves in passing through the system. In such an embodiment the pipe or tube can include one or more anode and/or cathode. Such anodes and cathodes can be in the form of an electrode that intrudes into the path of fluid flow. Alternatively, such anodes and cathodes can be integrated into or form part of a wall of the pipe or tube. In still other embodiments such anodes and cathodes can have a cylindrical conformation similar to that of the pipe or tube, but having a smaller diameter and positioned centrally within the pipe or tube. In a preferred embodiment the electrolytic cell is provided as a coiled pipe or tube having a first diameter, within which at least one anode and at least one cathode are provided in the form of cylinders having second and third diameters that are smaller than the first diameter. In such an embodiment an anode and cathode pair can be provided as set of nesting cylinders arranged around a common central axis, with one of either the anode and cathode having a smaller diameter than the other member of the pair. In some embodiments such an electrolytic cell can be provided with 2 more sets of concentrically arranged anode/cathode pairs. It should be appreciated that the polarity of an electrical potential applied to an anode/cathode pair of an electrolytic cell of a system of the inventive concept can be reversed while in use (e.g. through the application of electrical potential as a waveform).

As noted above, in some embodiments the nanobubble generator is provided with a gas in addition to the circulating fluid. Such a gas can be provided from a reservoir (such as a pressurized tank) or generated in situ (for example, by electrolysis or treatment of air with zeolites). Suitable gases include air, $O_2$, $H_2$, and $N_2$. Such gases can be incorporated into nanobubbles and hence into nanoplasmoids of nanoplasmoid bubbles.

Figure 4:
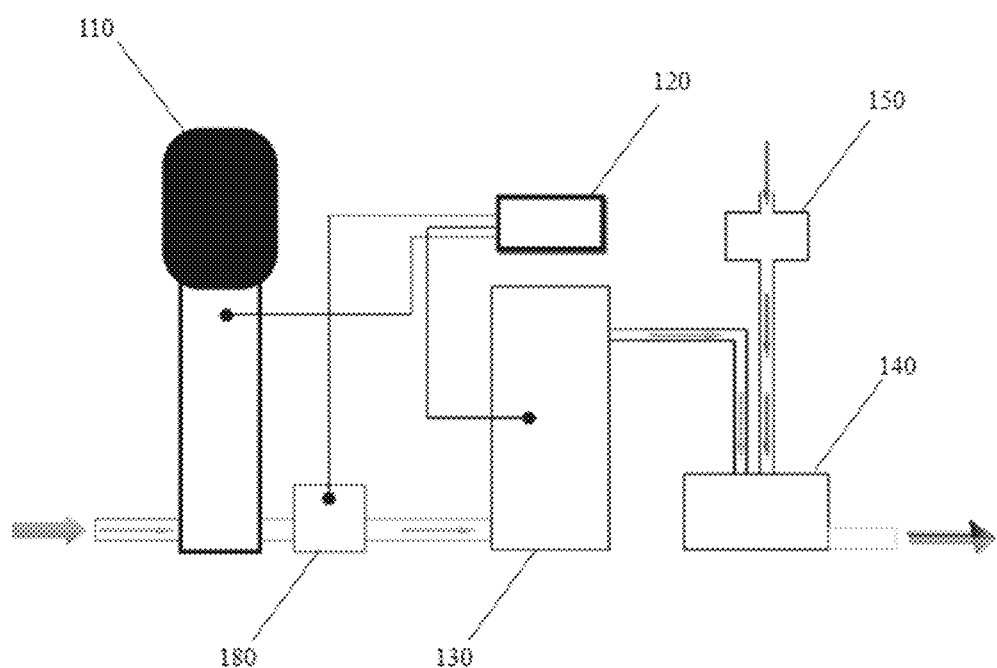
FIG. 4 depicts an embodiment of a system of the inventive concept that includes an electrical field source and a nanobubble/nanoplasmoid generator.

Another embodiment of a system of the inventive concept is shown in FIG. 4. As shown, the system includes a nanobubble/nanoplasmoid generator (140), a source of an electrical field (180), and an electrolytic cell (130). A power supply (120) is provided that can supply power to an electrolytic cell (130), an electrical field source (180), and/or a pump (110). Fluid, impelled by a pump (110) that provides a pressure differential, moves the electrical field generated by the electrical field source (180), an electrolytic cell (130), and a nanobubble/nanoplasmoid generator (140), which can optionally include an input (150) for a gas. Suitable sources for the electrical field can be plates (such as a capacitor), coils, and other electrode configurations. A controller can be used to modulate the applied electrical field. In such embodiments the electrical field can be applied continuously, periodically, and/or varied in a systematic manner, for example applying the electrical field at varying strengths and/or polarization over time. Such variations can be periodic, for example with electrical field strength and/or polarization oscillating as a waveform. Suitable waveforms include sinusoidal or sigmoidal waves, stepped wave functions, or combinations thereof.

As noted above, such embodiments that include an electrical field source can include an electrolytic cell. Suitable electrolytic cells can include a cathode and an anode, which are arranged so that the products of electrolysis (for example, $O_2$, $H_2$, OH–, OH⁻, H+, etc.) are released into the circulating fluid. Such species can react with one another to generate other species, for example peroxides. In some embodiments an electrolyte, such as NaCl, can be included in the fluid and be acted upon by the electrolytic cell to produce species derived from the electrolyte (such as HCl, NaOH, $Cl_2$, etc.). In some embodiments of the inventive concept the system or device can include a sensor that detects or quantifies species produced by the electrolytic cell, and a controller that receives data from the sensor. In such embodiments the presence and/or concentration of a product of electrolysis can be monitored using the sensor, with such data monitored by the controller which in turn modulates the power supplied to the electrolytic cell in order to maintain the rate of electrolysis within a desired range. For example, a pH monitor can be used to determine the amount of OH– and/or H+ present in the circulating fluid, and the power supplied to the electrolytic cell modulated to maintain the pH within a desired range. Products of the electrolysis of electrolytes or salts present in the circulating fluid can be monitored in a similar fashion.

The cathode and/or anode of the electrolytic cell can be arranged so that species produced by only one of the cathode or anode are released into circulating fluid. It should be appreciated that such species, notably charged species, can accumulate on the surface of nanobubbles and nanobubble plasmoids and enhance stability through charge repulsion. Electrodes of the electrolytic cell can be made of any suitable material, including stainless steel, copper, bronze, gold, silver, platinum, and conductive polymers. Such materials can enter the circulating fluid during electrolytic processing and be subsequently integrated into nanoplasmoid bubbles. In some embodiments the output from the nanobubble generator is coupled to the fluid input of the electrolytic cell, channeling some or all of the output back through the system.

An electrolytic cell utilized in a system of the inventive concept can have any suitable configuration. For example, an electrolytic cell can be configured as a reservoir that includes at least one anode and at least one cathode. Such an anode or cathode can be configured as plate, coil, rod, disc, sphere, or any suitable shape. Alternatively, an electrolytic cell can be configured as a pipe or tube through which fluid moves in passing through the system. In such an embodiment the pipe or tube can include one or more anode and/or cathode. Such anodes and cathodes can be in the form of an electrode that intrudes into the path of fluid flow. Alternatively, such anodes and cathodes can be integrated into or form part of a wall of the pipe or tube. In still other embodiments such anodes and cathodes can have a cylindrical conformation similar to that of the pipe or tube, but having a smaller diameter and positioned centrally within the pipe or tube. In a preferred embodiment the electrolytic cell is provided as a coiled pipe or tube having a first diameter, within which at least one anode and at least one cathode are provided in the form of cylinders having second and third diameters that are smaller than the first diameter. In such an embodiment an anode and cathode pair can be provided as set of nesting cylinders arranged around a common central axis, with one of either the anode and cathode having a smaller diameter than the other member of the pair.

As noted above, in some embodiments the nanobubble generator is provided with a gas in addition to the circulating fluid. Such a gas can be provided from a reservoir (such as a pressurized tank) or generated in situ (for example, by electrolysis or treatment of air with zeolites). Suitable gases include air, $O_2$, $H_2$, and $N_2$. Such gases can be incorporated into nanobubbles and hence into nanoplasmoids of nanoplasmoid bubbles.

Additional embodiments of systems of the inventive concept can incorporate elements of the systems described in FIGS. 1A, 1B, 2, 3, and 4. For example, a system can include an electrolytic cell and a transducer in addition to a nanobubble generator and a source of pressure differential. Similarly, a system can include an electrolytic cell, a magnetic field source, and a transducer in addition to a nanobubble generator and a source of pressure differential. In other embodiments, a system can include an electrolytic cell, an electrical field source, and a transducer in addition to a nanobubble generator and a source of pressure differential. In yet other embodiments, a system can include an electrolytic cell, an electrical field source, and a magnetic field source in addition to a nanobubble generator and a source of pressure differential.

In some embodiments of the inventive concept the system includes a reservoir that receives a fluid suspension of nanobubbles and/or nanoplasmoids from a system output and returns some or all of the fluid suspension to the system for re-processing. Such a reservoir advantageously permits recycling of the treated fluid and generation of high concentrations of nanobubbles/nanoplasmoids. In embodiments where the system is being utilized for therapeutic purposes such a reservoir can be configured to submerge all or part of an individual in need of treatment. For example, such a reservoir can be in the form of a therapeutic bath in which an individual can submerge a limb in need of treatment, or submerge themselves entirely or nearly entirely. Such a reservoir can additionally include components that increase patient comfort, such as a heater to adjust the temperature of the treated fluid and/or a recirculating pump that directs the treated fluid from outlets in the form of therapeutic 'jets'.

It should be appreciated that systems of the inventive concept can include additional features, such as mechanisms for the addition of salts and/or other chemical compounds to the fluid being treated. Suitable salts include sodium salts, calcium salts, magnesium salts, ferric salts, and ferrous salts. Suitable chemical compounds include emollients, skin moisturizers, surfactants, detergents, oxidizing agents (such as peroxides), reducing agents, and pharmaceutical compounds.

Figure 5:
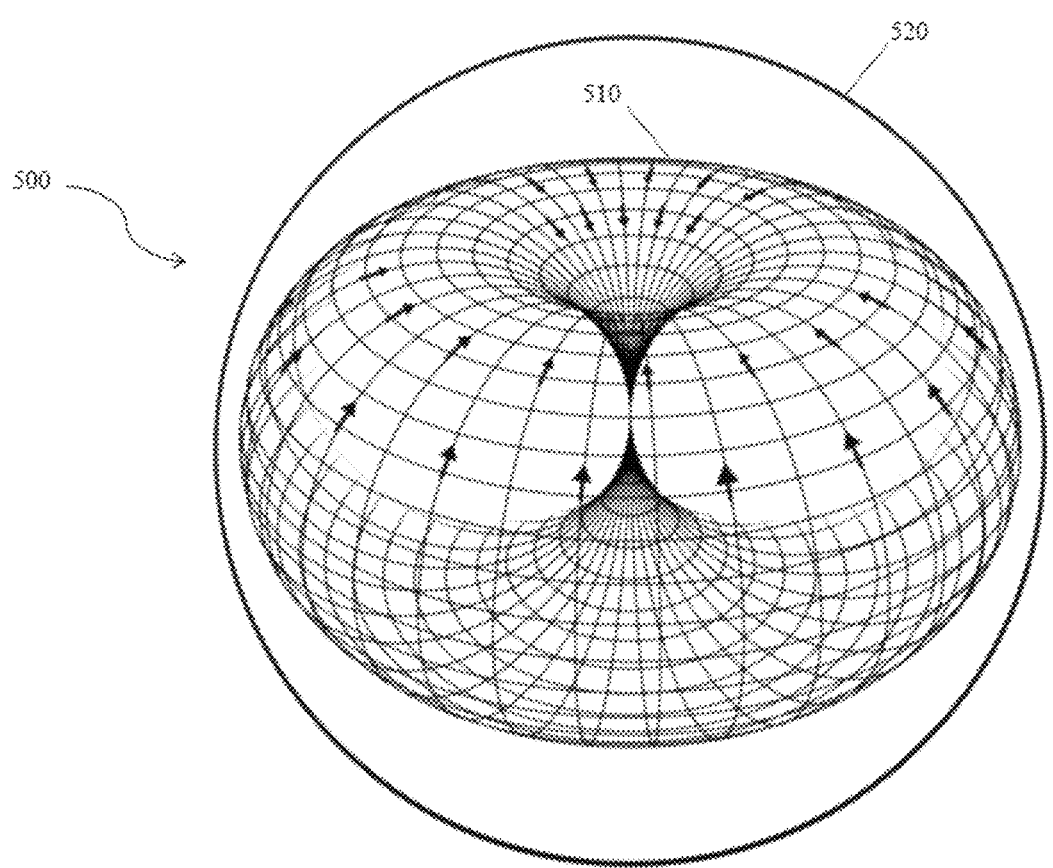
FIG. 5 depicts a nanoplasmoid bubble as produced by systems and methods of the inventive concept.

As noted above, systems of the inventive concept can include a nanobubble generator. In some embodiments nanoplasmoid generation occurs within the nanobubble generator; in such instances the nanobubble generator is equivalent to a nanoplasmoid generator. Within the context of this application a nanobubble is understood to be a bubble having a mean diameter of less than 1 µm. Similarly, a nanoplasmoid is understood to be a plasmoid having a mean maximum diameter of less than 1 µm. In preferred embodiments of the inventive concept a nanoplasmoid has a toroidal shape, and is encapsulated within a nanobubble as a nanoplasmoid bubble that is suspended within a liquid. A schematic depiction of such a nanoplasmoid is shown in FIG. 5, which shows a nanoplasmoid bubble (500) that includes a nanobubble (520) that encapsulates at least one nanoplasmoid (510).

Figure 6A:
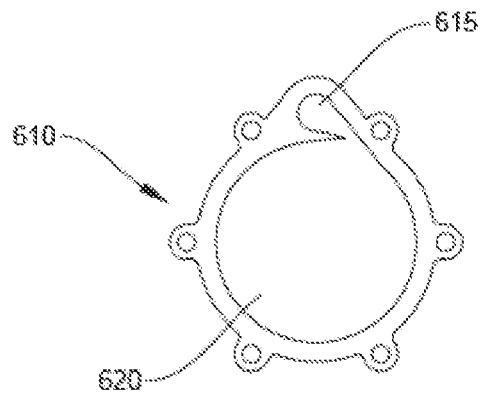
FIGS. 6A and 6B depict a vortex mixing plate of a nanobubble/nanoplasmoid generator of the inventive concept.
Figure 6B:
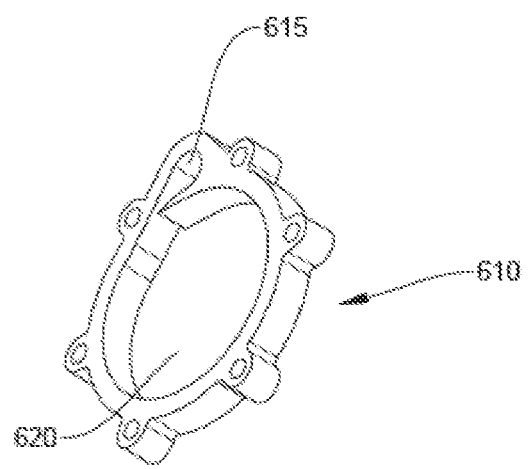

Nanobubble/nanoplasmoid generators utilized in systems and methods of the inventive concept can have a modular construction, and include two or more mixing plates. Each mixing plate has a substantially planar aspects and incorporates features that apply physical stress to a fluid flowing through the nanobubble/nanoplasmoid generator. An example of such a mixing plate is a vortex mixing plate, and example of which is shown in FIGS. 6A and 6B. FIG. 6A depicts a cross section of an example of a vortex mixing plate (610). FIG. 6B depicts an orthogonal view of an example of a vortex mixing plate (610). Such a plate includes an inlet portion (615) that reduces in size towards a narrow outlet. Such a narrow outlet can have a minimum dimension of about 0.1 µm, about 0.2 µm, about 0.5 µm, about 0.8 µm, about 1 µm, about 2 µm, about 5 µm, about 8 µm, about 10 µm, about 20 µm, about 50 µm, about 80 µm, about 0.1 mm, about 0.2 mm, about 0.5 mm, about 0.8 mm, about 1 mm, about 2 mm, about 5 mm, about 8 mm, about 10 mm, of more than about 10 mm. The narrow outlet is arranged tangentially to a central cavity (620), which can be circular. The inlet portion can be ovoid, partially ovoid, or foliate, and in some embodiments is asymmetrical. This arrangement imparts a swirling or circular motion to fluid entering the central cavity. Passage through the narrow outlet, transition to the relatively low pressure environment of the central cavity, and rotational movement within the cavity facilitate the formation of nanobubbles and/or nanoplasmoid bubbles. It should be appreciated that such vortex mixing plates can be mounted within an assembled nanobubble/nanoplasmoid generator in different orientations, so as to produce circular flow in different directions.

Figure 7A:
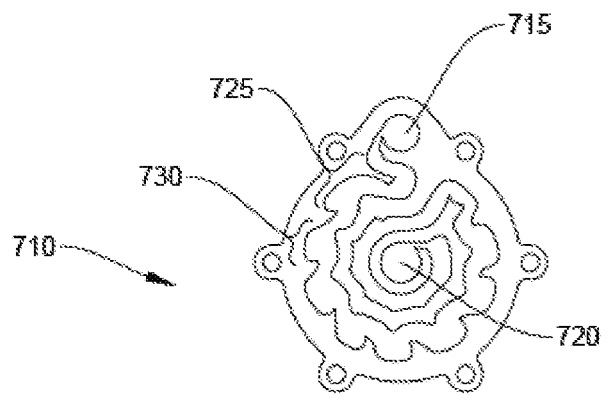
FIGS. 7A and 7B depict a shear mixing plate of a nanobubble/nanoplasmoid generator of the inventive concept.
Figure 7B:
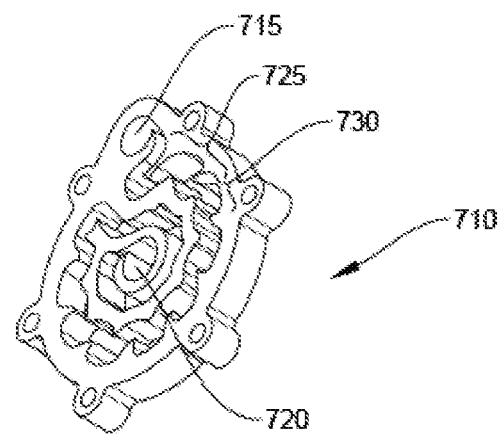

Another example of a mixing plate is a shear mixing plate. An example of a shear mixing plate is shown in FIGS. 7A and 7B. FIG. 7A depicts a cross section of a shear mixing plate (710). FIG. 7B depicts an orthogonal view of a shear mixing plate (710). A shear mixing plate can include an inlet (715, 720) and an outlet (720, 715) that are joined by a series of two or more shear mixing segments (725, 730). Each shear mixing segment includes a narrow inlet and a narrow outlet that are joined by an expansion region. Arranged in series, the narrow outlet of one shear mixing segment is connected to the narrow inlet of the subsequent shear mixing segment. In a preferred embodiments the linked shear mixing segments are arranged in a serpentine, coiled, or spiral arrangement that connects the inlet to the outlet. In some embodiments the inlet (715) is located near the periphery of the shear mixing plate and the outlet (720) is located centrally. In other embodiments the outlet (720) is located near the periphery of the shear mixing plate and the inlet (715) is located centrally.

Figure 8A:
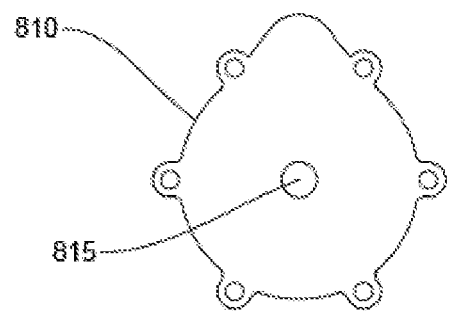
FIGS. 8A and 8B depict distribution plates of a nanobubble/nanoplasmoid generator of the inventive concept.
Figure 8B:
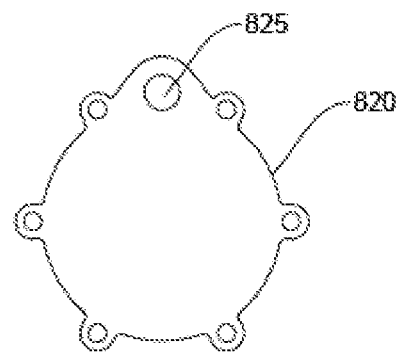

As noted above, a nanobubble/nanoplasmoid generator of the inventive concept can be constructed from a number of such mixing plates assembled in a modular fashion. In a preferred embodiment one or more center mixing plate(s) and one or more shear mixing plate(s) is used. In the final assembly the mixing plates can be selected, ordered, and oriented as needed for the scale of the system. In some embodiments, in the assembled nanobubble/nanoplasmoid generator adjacent center and/or shear mixing plates are separated by a distribution plate (810, 820). Such a distribution plate (810, 820) can have a central opening (815) (see FIG. 8A) or a peripheral opening (825) (see FIG. 8B), wherein such opening permit the passage of fluid.

Figure 9A:
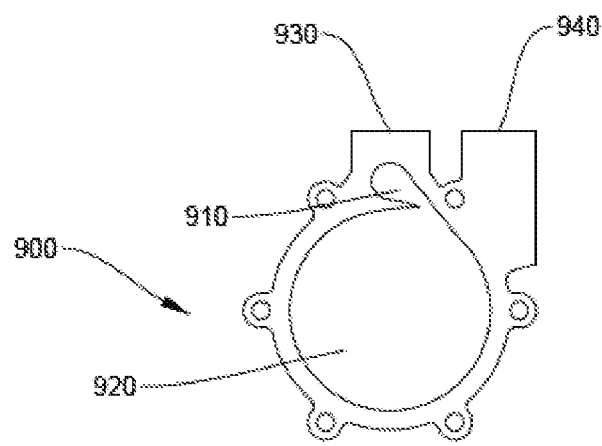
FIGS. 9A and 9B depict an inlet plate of a nanobubble/nanoplasmoid generator of the inventive concept.
Figure 9B:
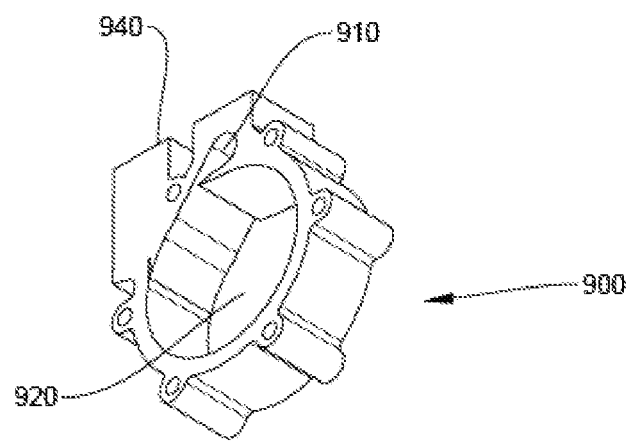

A nanobubble/nanoplasmoid generator can include an inlet plate (900), which can include features of the vortex mixing plate, such as an foliate inlet (910) and a central cavity (920) in addition to an inlet for fluid from outside of the assembled nanobubble/nanoplasmoid generator. In some embodiments, such as shown in FIGS. 9A and 9B, an inlet plate (900) can support two fluid inlets (930, 940) and can be utilized in a nanobubble/nanoplasmoid generator that includes two different sets of mixing plates. In such embodiments one fluid inlet can be used to introduce a liquid while the remaining fluid inlet is used to introduce a gas. FIG. 9A shows a cross section of an example of such an inlet plate. FIG. 9B shows an orthogonal view of an example of such an inlet plate.

Figure 10A:
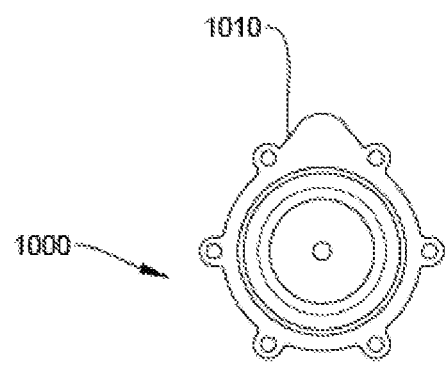
FIGS. 10A, 10B, and 10C depict a nozzle of a nanobubble/nanoplasmoid generator of the inventive concept.
Figure 10B:
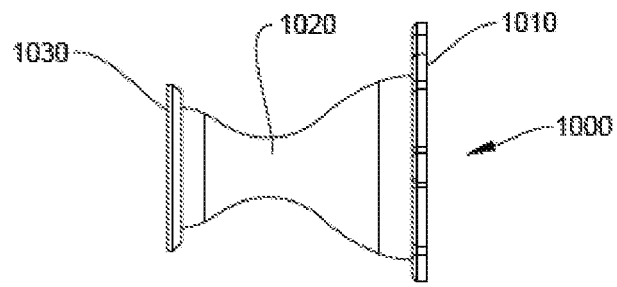
Figure 10C:
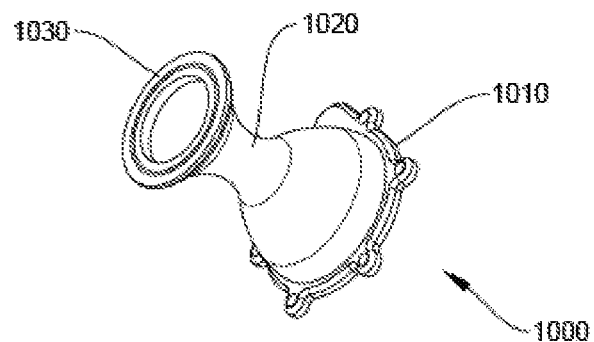

In still other embodiments a nanobubble/nanoplasmoid generator can terminate in a nozzle assembly (1000). An example of a nozzle assembly is shown in FIGS. 10A, 10B, and 10C. Such a nozzle assembly (1000) provides an expansion chamber (1010), which narrows to a constriction (1020) that subsequently opens to a flared outlet (1030). FIG. 10A shows an example of a nozzle assembly in an end-on view. FIG. 10B shows an example of a nozzle assembly in a side view. FIG. 10C shows an orthogonal view of such a nozzle assembly.

Figure 11:
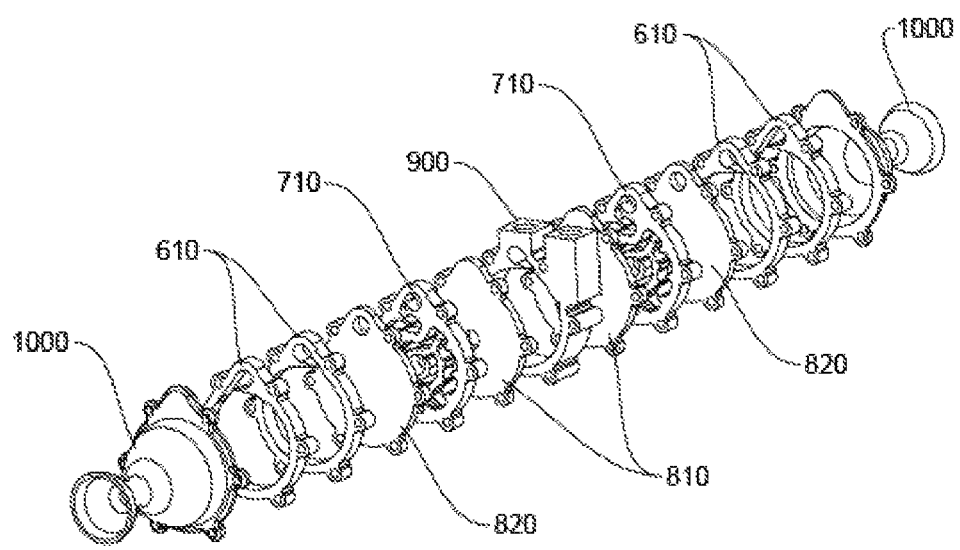
FIG. 11 depicts an exploded view of a nanobubble/nanoplasmoid generator of the inventive complex. The nanobubble/nanoplasmoid generator is configured as with a duplicate arrangement of mixing and distribution plates, arranged in mirror symmetry around a single inlet plate.
Figure 12:
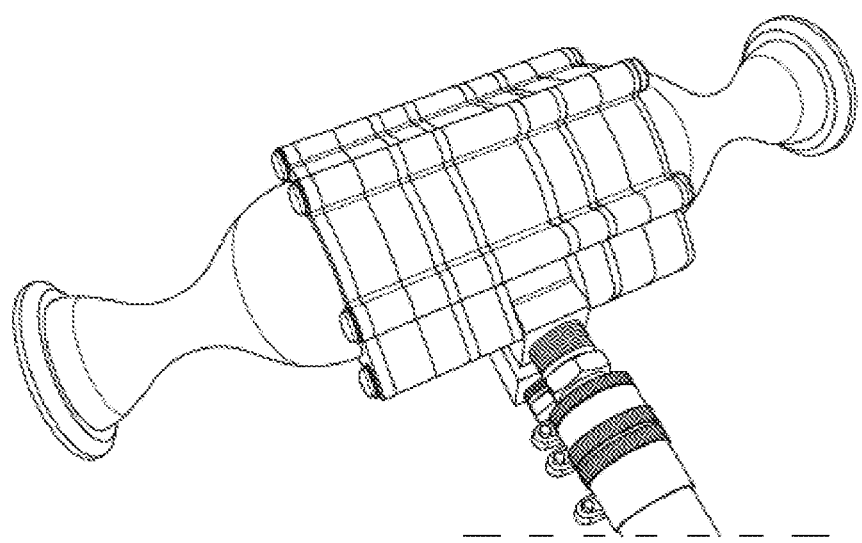
FIG. 12 depicts an assembled nanobubble/nanoplasmoid generator of the inventive concept.

As noted above, a nanobubble/nanoplasmoid generator of the inventive concept can be of modular design, assembled from components as described above. In a preferred embodiment the nanobubble/nanoplasmoid generator includes two sets of mixing plate components, arranged in a symmetrical manner to provide a dual system An exploded view of such an embodiment is shown in FIG. 11, with individual elements labeled as in FIGS. 6A, 6B, 7A, 7B, 8A, 8B, 9A, 9B, 10A, 10B, and 10C. As shown, a single centrally placed inlet plate is in fluid communication with shear mixing plates on each side via a set of distribution plates that each have a central opening. Each of these shear mixing plates is in turn in fluid communication with a corresponding vortex mixing plate via a distribution plate with a peripheral opening. Each of these vortex mixing plates is in fluid communication with another vortex mixing plate of opposing orientation, and the final vortex mixing plate is coupled to a nozzle assembly. A photograph of an assembled nanobubble/nanoplasmoid generator with fluid lines coupled to the fluid inlets is shown in FIG. 12.

Although depicted in FIG. 11 with a duplicate set of 3 mixing plates, it should be appreciated that the modular construction of the nanobubble/nanoplasmoid generator permits a wide variety of configurations. Inventors contemplate that a nanobubble/nanoplasmoid generator of the inventive concept can incorporate from 3 mixing plates to 3,000 or more mixing plates, as necessary.

In operation, a fluid (for example, water) is introduced into a nanobubble/nanoplasmoid generator of the system at a pressure differential of from 40 psi ($2.8 \times 10^6$ Pa) to 40,000 psi ($2.8 \times 10^9$ Pa). This can be accomplished using a conventional pump, for example a pump configured for use with a commercial reverse osmosis system. At the same time, a gas (such as air, $O_2$, $H_2$, electrolysis products, etc.) is introduced into the nanobubble/nanoplasmoid generator at a similar pressure differential of from 40 psi ($2.8 \times 10^6$ Pa) to 40,000 psi ($2.8 \times 10^9$ Pa). Flow rates and/or pressures of the applied fluid and gas can be modulated or controlled during nanoplasmoid bubble generation, for example in order to provide a nanoplasmoid bubbles in desired numbers or having a desired size and/or content. Flow rate and/or pressures can be adjusted manually or by using a control mechanism. Such adjustments can be made in response to data from sensors, for instance an optical density sensor, optical scatter sensor, zeta-potential sensor, pH sensor, conductivity sensor, and/or chemical species sensor. It should be appreciated that excess gas (i.e. gas not incorporated into nanoplasmoid bubbles) can be captured and returned to the nanobubble/nanoplasmoid generator.

Fluid containing nanoplasmoid bubbles (i.e. nanoplasmoid bubble suspension) is directed to a reservoir, which can be configured for treatment of patients. The collected nanoplasmoid bubble suspension can be directed from the reservoir back to the system for additional processing. This recycling of the nanoplasmoid bubble suspension provides additional control over the composition and size of the suspended nanoplasmoid bubbles, as well as providing control over the number of nanoplasmoid bubbles per mL of such a suspension. This recycling can be performed for periods ranging from 1 minute to 8 hours. Typically recycling can be performed for about 1 hour.

Figure 13A:
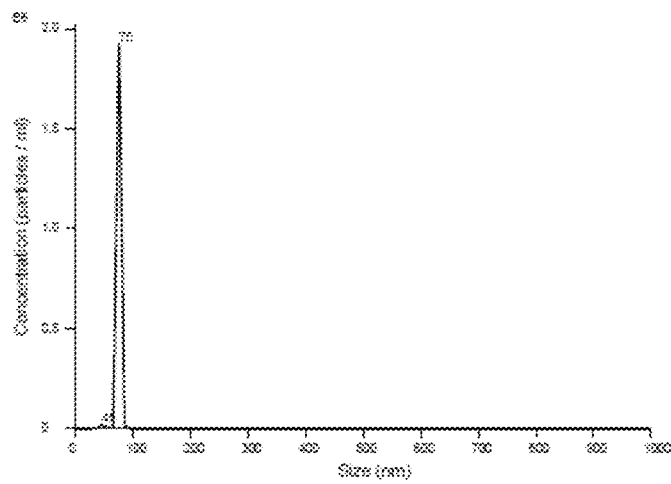
FIGS. 13A and 13B depict the effect of treatment of distilled water using a nanobubble/nanoplasmoid generator of the inventive concept.
Figure 13B:
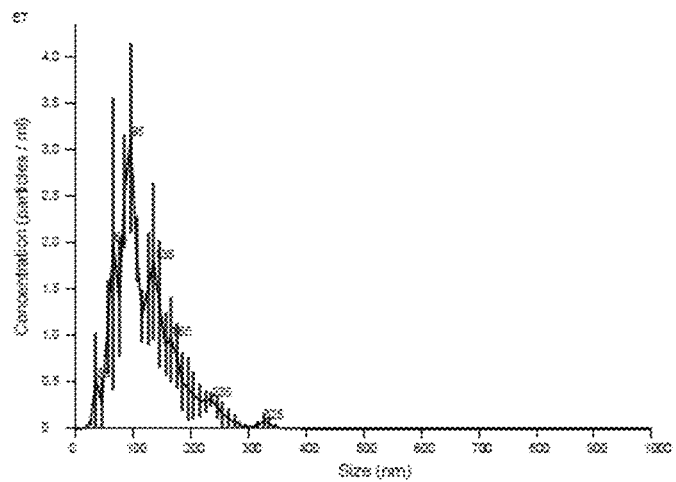

In typical use, a system of the inventive concept configured as shown in FIGS. 1A and 1$n$ which recycling of the nanoplasmoid bubble suspension prepared using deionized water was performed for 50 minutes provided up to $2.4 \times 10^8$ nanoplasmoid bubbles per mL of suspension. Samples taken prior to treatment (FIG. 13A) and after such treatment (FIG. 13B) show that the nanoplasmoid bubbles generated have the following characteristics:

Mean diameter: 119.4 nm
Standard Deviation: 53.1 nm
Mode of distribution: 93.2 nm The Applicant notes that both the mean diameter and standard deviation of said diameter of the nanoplasmoid bubbles so produced are significantly smaller than those of nanobubbles produced by prior art apparatus under similar conditions.

As noted above, nanoplasmoid bubble suspensions produced by systems of the inventive concept have been found to have therapeutic uses. Without wishing to be bound by theory, the inventors believe that therapeutic effects are provide by both species generated during nanoplasmoid bubble generation (for example, peroxides, $O_3$, $H_2$, etc.) and physical properties of the nanoplasmoid bubbles so generated, which enhance perfusion into tissues. Benefits can be realized by consumption of the nanoplasmoid bubble suspension (i.e. by drinking as a beverage) and/or by immersion in the nanoplasmoid bubble suspension. Surprisingly, Inventors have found that immersion in a nanoplasmoid bubble suspension can provide improvement in systemic and/or topical disease states. Inventors have found that numerous skin conditions (including topical fungal infections, slow-healing wounds, wrinkles, abnormally dry skin, eczema, psoriasis, and skin carcinoma) can be reduced or eliminated by topical treatment with a nanoplasmoid bubble suspension as generated by a system of the inventive concept. Such improvement can be realized using a treatment schedule of daily exposure to a nanoplasmoid bubble suspension for a period of at least 20 minutes, at intervals of from three times a day to once a week, and/or for a period of about 30 to 90 days.

Other uses of nanoplasmoid bubble suspensions include sanitization and/or disinfection of surfaces and equipment (for example, medical and dental equipment, personal care items, food preparation equipment, etc.). Nanoplasmoid bubble suspension can also be utilized to purify contaminated water, for example by removal and/or oxidation of organic molecules, flotation and subsequent removal of particulates, and/or enhancement of natural (for example, biological) breakdown processes. Similarly, the introduction of nanoplasmoid bubbles into commercial organic liquids (such as industrial lubricants) can prevent or retard decomposition of such liquids. In some embodiments, nanoplasmoid bubble suspensions are used to treat the surface of a material, for example by partial or complete immersion or by application of a stream, spray, and/or mist that includes nanoplasmoid bubbles. Such treatment can, for example remove a biofilm from a surface, and/or prevent or retard its formation.

In other embodiments, consumption of a beverage or food that includes nanoplasmoid bubbles can modify aspects of an animal's body chemistry in a beneficial fashion. For example, consumption of a liquid that includes a nanoplasmoid bubble suspension by birds can reduce the content of toxic ammonia found in their droppings. This reduction simplifies care of domestic fowl and improves local environmental conditions.

In some embodiments of the inventive concept, a system is provided in which a nanoplasmoid bubble generator as described above is fluidically coupled with a secondary functional system, such that a nanoplasmoid bubble suspension is provided to the secondary functional system that aids in its function. For example, a nanoplasmoid bubble generator of the inventive concept can be fluidically coupled with a water sanitation or filtration system, thereby reducing fouling and improving the sanitation function. Suitable secondary functional systems include a water filtration system, a water purifying system (e.g. a system for producing potable water), a desalination system, a water heating system, a steam generator, a water cooling system, a sanitation system, a power washer, a laundry cleaning system, a dishwasher, a car wash, and/or a vacuum cleaner. In some instances the use of a nanoplasmoid bubble suspension in such systems improves their capabilities in providing their respective functions. In other instances the nanoplasmoid bubble suspension can be used to treat materials dislodged during cleaning and/or other waste generated by the secondary functional system.

In other embodiments of the inventive concept, a nanoplasmoid bubble suspension as described above is utilized in a manufacturing process. In some embodiments the nanoplasmoid bubble suspension is utilized in the manufacture of liquid chemical products, such as paint, nail polish, perfumes and/or colognes, fuels, industrial (e.g. non-edible) oils, and cleaning products. In other embodiments the nanoplasmoid bubble suspension is utilized in the manufacture of consumable products, such as foods, beverages, alcohol, edible oils, proteins, and ice.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A system for generating a nanobubble/nanoplasmoid suspension, comprising:
    an electrolytic cell;
    a nanobubble/nanoplasmoid generator configured to form a suspension of a second fluid in a first fluid wherein elements of the second fluid in the suspension have a mean diameter of less than 1 μm, and that is fluidically coupled to the electrolytic cell; and
    a source of a pressure differential that is in fluid communication with the electrolytic cell and the nanobubble/nanoplasmoid generator,
    wherein the source of the pressure differential is positioned and configured to move the first fluid through the system,
wherein the nanobubble/nanoplasmoid generator comprises:
    a first vortex mixing plate comprising a first central circular cavity and a first aperture in fluid communication with the first central circular cavity, wherein the first aperture is configured as an asymmetric folium having a first narrow terminus, wherein the first narrow terminus is oriented in a first radial direction relative to the first central circular cavity;
    a shear mixing plate comprising a second aperture that is in fluid communication with the first central circular cavity, wherein the second aperture comprises a second narrow terminus, wherein the second narrow terminus is fluidically coupled to a shear mixing segment, wherein the shear mixing segment comprises a first shear region comprising a first narrow inlet, a first expansion region, and a first narrowed outlet and a second shear region comprising a second narrow inlet fluidically coupled to the first narrow outlet, a second expansion region, and a second narrow outlet;
    a second vortex mixing plate comprising a second central circular cavity and a third aperture in fluid communication with the first shear mixing plate and the second central circular cavity, wherein the third aperture is configured as an asymmetric folium having a third narrow terminus, wherein the third narrow terminus is oriented in a second radial direction relative to the second central circular cavity;
    a third center vortex plate comprising a third central circular cavity and a fourth aperture in fluid communication with the second central circular cavity and the third central circular cavity, wherein the fourth aperture is configured as an asymmetric folium having a fourth narrow terminus, wherein the fourth narrow terminus is oriented in a third radial direction relative to the third central circular cavity, and wherein the third radial direction is in opposition to the second radial direction; and,
    an inlet plate in fluid communication with a source of a first fluid, a source of a second fluid, and the first vortex mixing plate.

2. The system of claim 1, wherein the first fluid is a liquid and the second fluid is a gas.

3. The system of claim 1, wherein the shear mixing plate comprises a plurality of shear mixing segments, wherein the plurality of shear mixing segments is serially arranged such that, with the exception of a terminal shear mixing segment, each of the second narrow outlets is fluidically coupled to the first narrow outlet of a subsequent one of the plurality of shear mixing segments, and wherein the plurality of shear mixing segments are arranged in a spiral fashion.

4. The system of claim 1, wherein the first vortex mixing plate is juxtaposed with a first distribution plate comprising a first port, and wherein the first distribution plate is juxtaposed with the shear mixing plate.

5. The device of claim 1, wherein the shear mixing plate is juxtaposed with a second distribution plate comprising a second port, and wherein the second distribution plate is juxtaposed with the second vortex mixing plate.

6. The system of claim 1, wherein the second vortex mixing plate is juxtaposed with a third distribution plate comprising a third port, and wherein the third distribution plate is juxtaposed with the third vortex mixing plate.

7. The system of claim 1, wherein the third center mixing plate is in fluid communication with a nozzle.

8. The system of claim 7, wherein the nozzle comprises an expansion chamber that is in fluid communication with the third center mixing plate, a nozzle outlet, and a central constriction interposed between the expansion chamber and the nozzle outlet.

9. The system of claim 1, further comprising a field source, wherein the field source is configured to generate a field that intersects the first fluid.

10. The system of claim 9, wherein the field source is an electrical field source.

11. The system of claim 9, wherein the field source is a magnetic field source.

12. The system of claim 9, further comprising a controller that is communicatively coupled to the field source and configured to modulate the field.

13. The system of claim 12, wherein the modulation comprises application of a waveform.

14. The system of claim 1, further comprising a reservoir that receives a nanoplasmoid bubble suspension from the nanobubble/nanoplasmoid generator.

* * * * *